United States Patent

Borzatta et al.

[11] Patent Number: 5,610,211
[45] Date of Patent: Mar. 11, 1997

[54] 2,2,6,6-TETRAMETHYLPIPERIDINE DERIVATIVES FOR USE AS STABILIZING AGENTS FOR ORGANIC MATERIALS

[75] Inventors: Valerio Borzatta; Roberto Scrima, both of Bologna, Italy

[73] Assignee: Ciba-Geigy Corporation, Tarrytown, N.Y.

[21] Appl. No.: 552,043

[22] Filed: Nov. 2, 1995

[30] Foreign Application Priority Data

Nov. 9, 1994 [IT] Italy ................. MI94A002260

[51] Int. Cl.⁶ ............... C08K 5/3492; C07D 403/00
[52] U.S. Cl. ............................. 524/100; 544/198
[58] Field of Search ................. 524/100; 544/198

[56] References Cited

U.S. PATENT DOCUMENTS

| | | | |
|---|---|---|---|
| 4,108,829 | 8/1978 | Cassandrini et al. | 260/45.8 |
| 4,477,615 | 10/1984 | Rasparti et al. | 544/198 |
| 4,698,381 | 10/1987 | Minagawa et al. | 544/198 |
| 4,816,507 | 3/1989 | Cantatore et al. | 524/100 |
| 4,833,870 | 11/1989 | Cantatore et al. | 544/198 |
| 4,927,930 | 5/1990 | Cantatore et al. | 544/198 |
| 4,933,451 | 6/1990 | Cantatore et al. | 544/198 |
| 4,997,938 | 3/1991 | Cantatore et al. | 544/198 |
| 5,180,762 | 1/1993 | Canova | 544/198 |

FOREIGN PATENT DOCUMENTS

| | | |
|---|---|---|
| 0292437 | 11/1988 | European Pat. Off. . |
| 0345220 | 12/1989 | European Pat. Off. . |
| 0376886 | 7/1990 | European Pat. Off. . |
| 0479724 | 4/1992 | European Pat. Off. . |
| 0523007 | 1/1993 | European Pat. Off. . |
| 0634412 | 1/1995 | European Pat. Off. . |
| 5738589 | 8/1982 | Japan . |
| 2194237 | 3/1988 | United Kingdom . |

*Primary Examiner*—Veronica P. Hoke
*Attorney, Agent, or Firm*—Luther A. R. Hall

[57] ABSTRACT

Compounds of the formula (I)

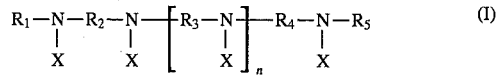

in which n is zero or 1, X denotes a group of formula (II),

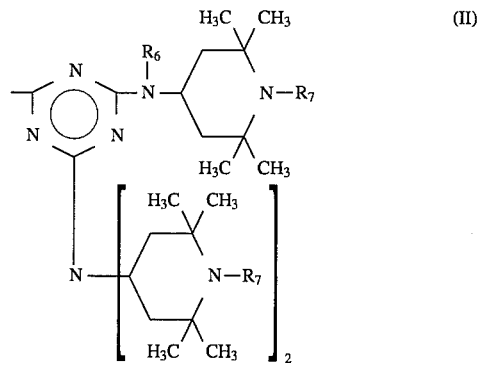

$R_1$ and $R_5$ are e.g. hydrogen, $R_2$, $R_3$ and $R_4$, which may be identical or different, are $C_2$–$C_{12}$alkylene, $R_6$ is e.g. hydrogen or $C_1$–$C_{18}$alkyl and $R_7$ is e.g. hydrogen or $C_1$–$C_8$alkyl, are useful as stabilizers for organic materials against degradation induced by light, heat or oxidation.

12 Claims, No Drawings

2,2,6,6-TETRAMETHYLPIPERIDINE DERIVATIVES FOR USE AS STABILIZING AGENTS FOR ORGANIC MATERIALS

The present invention relates to new piperidine triazine compounds and their use as stabilizing agents for organic materials against light, heat and oxidation, in particular synthetic polymers, and to organic materials stabilized in this way.

The stabilization of synthetic polymers by means of triazine compounds containing 2,2,6,6-tetramethylpiperidine groups has been described in numerous patents, in particular in U.S. Pat. No. 4,108,829 and JP Patent Sho 57-38589 as well as U.S. Pat. No. 4,816,507 and U.S. Pat. No. 4,997,938.

The present invention relates to novel compounds of formula (I)

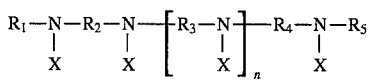

in which n is zero or 1 and X is a group of formula (II),

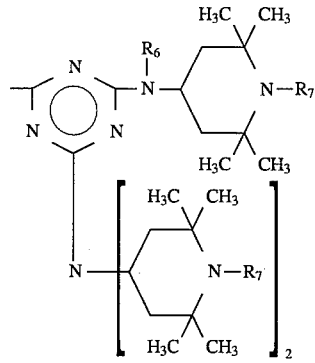

$R_1$ and $R_5$, which may be identical or different, are hydrogen, $C_1$–$C_{18}$alkyl, $C_5$–$C_{12}$cycloalkyl, unsubstituted or substituted with 1, 2 or 3 $C_1$–$C_4$alkyls; $C_7$–$C_9$phenylalkyl, unsubstituted or substituted on the phenyl with 1, 2 or 3 $C_1$–$C_4$alkyls; or $R_1$ and $R_5$ are a group of formula (III)

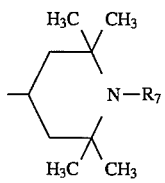

$R_2$, $R_3$ and $R_4$, which may be identical or different, are $C_2$–$C_{12}$alkylene;

$R_6$ is hydrogen, $C_1$–$C_{18}$alkyl, $C_5$–$C_{12}$cycloalkyl, unsubstituted or substituted with 1, 2 or 3 $C_1$–$C_4$alkyls; $C_3$–$C_6$alkenyl, $C_7$–$C_9$phenylalkyl, unsubstituted or substituted on the phenyl with 1, 2 or 3 $C_1$–$C_4$alkyls;

$R_7$ is hydrogen, $C_1$–$C_8$ alkyl, O, OH, $CH_2CN$, $C_1$–$C_{18}$alkoxy, $C_5$–$C_{12}$cycloalkoxy, $C_3$–$C_6$alkenyl, $C_7$–$C_9$phenylalkyl, unsubstituted or substituted on the phenyl with 1, 2 or 3 $C_1$–$C_4$alkyls; or $R_7$ is an aliphatic $C_1$–$C_8$acyl;

when n is 1 and $R_1$ and $R_5$ are a group of formula (III), X may also be a group of formula (IV)

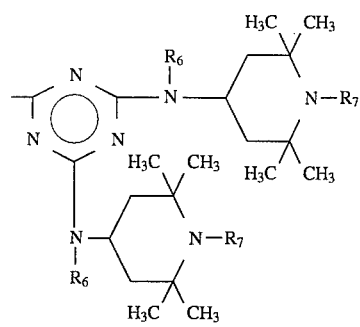

in which $R_6$ and $R_7$ are as defined above.

The following examples may be given of alkyl containing up to 18 carbon atoms: methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

The following examples may be given of $C_5$–$C_{12}$cycloalkyl, unsubstituted or substituted with 1, 2 or 3 $C_1$–$C_4$alkyls: cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Preference is given to unsubstituted or substituted cyclohexyl.

The following examples may be given of $C_7$–$C_9$phenylalkyl, unsubstituted or substituted on the phenyl with 1, 2 or 3 $C_1$–$C_4$alkyls: benzyl, methylbenzyl, dimethylbenzyl, trimethylbenzyl, t-butylbenzyl and 2-phenylethyl. Preference is given to benzyl.

The following examples are given of alkylene containing up to 12 carbon atoms: ethylene, propylene, trimethylene, 2-methyltrimethylene, 2,2-dimethyltrimethylene, tetramethylene, pentamethylene, hexamethylene, trimethylhexamethylene, octamethylene, decamethylene and dodecamethylene.

Examples of $C_3$–$C_6$alkenyl are allyl, 2-methylallyl, butenyl and hexenyl. Preference is given to alkenyls in which the carbon atom in position 1 is saturated; preference is given in particular to allyl.

The following examples are given of alkoxy containing up to 18 carbon atoms: methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. Preferred examples are $C_6$–$C_{12}$alkoxy, in particular heptoxy and octoxy.

Examples of $C_5$–$C_{12}$cycloalkoxy are cyclopentoxy, cyclohexoxy, cycloheptoxy, cyclooctoxy, cyclodecyloxy and cyclododecyloxy. Preference is given to cyclopentoxy and cyclohexoxy.

The following examples are given of aliphatic acyl containing up to 8 carbon atoms: acetyl, propionyl, butyryl, isobutyryl, pentanoyl, hexanoyl, heptanoyl, acryloyl and crotonyl. Preference is given to $C_1$–$C_8$alkanoyl and $C_3$–$C_8$alkenoyl.

Preferred definitions of $R_7$ are hydrogen, $C_1$–$C_4$alkyl, OH, $C_6$–$C_{12}$alkoxy, $C_5$–$C_8$cycloalkoxy, allyl, benzyl or acetyl, in particular hydrogen or methyl.

X is preferably a group of the formula (II).

Preferred compounds of formula (I) are those in which X is a group of formula (II), $R_1$ and $R_5$, which may be identical or different, are hydrogen, $C_1$–$C_{12}$alkyl, $C_5$–$C_7$cycloalkyl or $C_7$–$C_9$phenylalkyl; $R_2$, $R_3$ and $R_4$, which may be identical or different, are $C_2$–$C_6$alkylene and $R_6$ is hydrogen, $C_1$–$C_{12}$alkyl, $C_5$–$C_7$cycloalkyl, $C_3$–$C_6$alkenyl or $C_7$–$C_9$phenylalkyl.

Particularly preferred compounds of formula (I) are those in which X is a group of formula (II), $R_1$ and $R_5$, which may be identical or different, are hydrogen, $C_1$–$C_6$alkyl, cyclohexyl or benzyl; $R_2$, $R_3$ and $R_4$, which may be identical or different, are $C_2$–$C_6$alkylene and $R_6$ is hydrogen, $C_1$–$C_6$alkyl, cyclohexyl, allyl or benzyl.

Compounds of formula (I) of special interest are those in which X is a group of formula (II), $R_1$ and $R_5$, which may be identical or different, are hydrogen or $C_1$–$C_4$alkyl; $R_2$, $R_3$ and $R_4$, which may be identical or different, are $C_2$–$C_3$alkylene; $R_6$ is $C_1$–$C_4$ alkyl and $R_7$ is hydrogen or methyl.

Preferred compounds of formula (I) are also those in which n is 1, $R_1$ and $R_5$ are a group of formula (III) and X is a group of formula (IV).

Further preferred compounds of formula (I) are those in which n is 1, $R_1$ and $R_5$ are a group of formula (III); X is a group of formula (IV); $R_2$, $R_3$ and $R_4$, which may be identical or different, are $C_2$–$C_6$alkylene and $R_6$ is hydrogen, $C_1$–$C_{12}$alkyl, $C_5$–$C_7$cycloalkyl, $C_3$–$C_6$-alkenyl or $C_7$–$C_9$phenylalkyl.

Compounds of formula (I) of special interest are also those in which n is 1, $R_1$ and $R_5$ are a group of formula (III); X is a group of formula (IV); $R_2$, $R_3$ and $R_4$, which may be identical or different, are $C_2$–$C_6$alkylene and $R_6$ is hydrogen, $C_1$–$C_6$alkyl, cyclohexyl, allyl or benzyl.

Further particularly preferred compounds of formula (I) are those in which n is 1, $R_1$ and $R_5$ are a group of formula (III); X is a group of formula (IV); $R_2$, $R_3$ and $R_4$, which may be identical or different, are $C_2$–$C_3$alkylene; $R_6$ is $C_1$–$C_4$alkyl and $R_7$ is hydrogen or methyl.

Examples of compounds of formula (I) are:

$N^I,N^{II},N^{III}$-tris[2-(N-(2,2,6,6-tetramethylpiperidin-4-yl)-butylamino)-4-(bis[2,2,6,6-tetramethylpiperidin-4-yl]amino)-triazin-6-yl]-diethylenetriamine;

$N^I,N^{II},N^{III}$-tris[2-(N-(1,2,2,6,6-pentamethylpiperidin-4-yl)-butylamino)-4-(bis[1,2,2,6,6-pentamethylpiperidin-4-yl]amino)-triazin-6-yl]-diethylenetriamine;

$N^I,N^{II},N^{III}$-tris[2-(N-(2,2,6,6-tetramethylpiperidin-4-yl)-butylamino)-4-(bis[2,2,6,6-tetramethyl-piperidin-4-yl]amino)-triazin-6-yl]-dihexamethylenetriamine;

$N^I,N^{II},N^{III}$-tris[2-(N-(1,2,2,6,6-pentamethylpiperidin-4-yl)-butylamino)-4-(bis[1,2,2,6,6-pentamethylpiperidin-4-yl]amino)-triazin-6-yl]-dihexamethylenetriamine;

$N^I,N^{II},N^{III}$-tris[2-(N-(2,2,6,6-tetramethylpiperidin-4-yl)-ethylamino)-4-(bis[2,2,6,6-tetramethylpiperidin-4-yl]amino)-triazin-6-yl]-diethylenetriamine;

$N^I,N^{II},N^{III}$-tris[2-(N-(1,2,2,6,6-pentamethylpiperidin-4-yl)-ethylamino)-4-(bis[1,2,2,6,6-pentamethylpiperidin-4-yl]amino)-triazin-6-yl]-diethylenetriamine;

$N^I,N^{II},N^{III}$-tris[2-(N-(2,2,6,6-tetramethylpiperidin-4-yl)-ethylamino)-4-(bis[2,2,6,6-tetramethyl-piperidin-4-yl]amino)-triazin-6-yl]-dihexamethylenetriamine;

$N^I,N^{II},N^{III}$-tris[2-(N-(1,2,2,6,6,-pentamethylpiperidin-4-yl)-ethylamino)-4-(bis[1,2,2,6,6-pentamethylpiperidin-4-yl]amino)-triazin-6-yl]-dihexamethylenetriamine;

$N^I,N^{II},N^{III}$-tris[2-(N-(2,2,6,6-tetramethylpiperidin-4-yl)-dodecylamino)-4-(bis[2,2,6,6-tetramethylpiperidin-4-yl]amino)-triazin-6-yl]-diethylenetriamine;

$N^I,N^{II},N^{III}$-tris[2-(N-(1,2,2,6,6-pentamethylpiperidin-4- yl)-dodecylamino)-4-(bis[1,2,2,6,6-pentamethylpiperidin-4-yl]amino)-triazin-6-yl]-diethylenetriamine;

$N^I,N^{II},N^{III}$-tris[2-(N-(2,2,6,6-tetramethylpiperidin-4-yl)-dodecylamino)-4-(bis[2,2,6,6,-tetramethylpiperidin-4-yl]amino)-triazin-6-yl]-dihexamethylenetriamine;

$N^I,N^{II},N^{III}$-tris[2-(N-(1,2,2,6,6-pentamethylpiperidin-4-yl)-dodecylamino)-4-(bis[1,2,2,6,6-pentamethylpiperidin-4-yl]amino)-triazin-6yl]-dihexamethylenetriamine;

$N^I,N^{II},N^{III},N^{IV}$-tetrakis[2-(N-(2,2,6,6-tetramethylpiperidin-4-yl)-butylamino)-4-(bis[2,2,6,6-tetramethylpiperidin-4-yl]amino)-triazin-6-yl]-1,5,8,12-tetraazadodecane;

$N^I,N^{II},N^{III},N_{IV}$-tetrakis[2-(N-(1,2,2,6,6-pentamethylpiperidin-4-yl)-butylamino)-4-(bis 1,2,2,6,6-pentamethylpiperidin-4-yl]amino)-triazin-6-yl]-1,5,8,12-tetraazadodecane;

$N^I,N^{II},N^{III},N^{IV}$-tetrakis[2-(N-(2,2,6,6-tetramethylpiperidin-4-yl)-ethylamino)-4-(bis[2,2,6,6-tetramethylpiperidin-4-yl]amino)-triazin-6-yl]-1,5,8,12-tetraazadodecane;

$N^I,N^{II},N^{III},N^{IV}$-tetrakis[2-(N-(1,2,2,6,6-pentamethylpiperidin-4-yl)-ethylamino)-4-(bis[1,2,2,6,6-pentamethylpiperidin-4-yl]amino)-triazin-6-yl]-1,5,8,12-tetraazadodecane;

$N^I,N^{II},N^{III},N^{IV}$-tetrakis[2-(N-(2,2,6,6-tetramethylpiperidin-4-yl)-dodecylamino)-4-(bis[2,2,6,6-tetramethylpiperidin-4-yl]-amino)-triazin-6-yl]-1,5,8,12-tetraazadodecane;

$N^I,N^{II},N^{III},N^{IV}$-tetrakis[2-(N-(1,2,2,6,6-pentamethylpiperidin-4-yl)-dodecylamino)-4-(bis[1,2,2,6,6-pentamethylpiperidin-4-yl]amino)-triazin-6-yl]-1,5,8,1 2-tetraazadodecane;

$N^I,N^{IV}$-bis[2,2,6,6-tetramethylpiperidin-4-yl]-$N^I,N^{II},N^{III},N^{IV}$-tetrakis[2,4-bis[N-(2,2,6,6-tetramethylpiperidin-4-yl)-butylamino]-triazin-6-yl]-1,5,8,12-tetraazadodecane $N^I,N^{IV}$-bis[1,2,2,6,6-pentamethylpiperidin-4-yl]-$N^I,N^{II},N^{III},N^{IV}$-tetrakis[2,4-bis[N-(1,2,2,6,6-pentamethylpiperidin-4-yl)-butylamino]-triazin-6-yl]-1,5,8,12-tetraazadodecane;

$N^I,N^{IV}$-bis[2,2,6,6-tetramethylpiperidin-4-yl]-$N^I,N^{II},N^{III},N^{IV}$-tetrakis[2,4-bis[N-(2,2,6,6-tetramethylpiperidin-4-yl)-ethylamino]-triazin-6-yl]-1,5,8,12-tetraazadodecane;

$N^I,N^{IV}$-bis[1,2,2,6,6-pentamethylpiperidin-4-yl]-$N^I,N^{II},N^{III},N^{IV}$-tetrakis[2,4-bis[N-(1,2,2,6,6-pentamethylpiperidin-4-yl)-ethylamino]-triazin-6-yl]-1,5,8,12-tetraazadodecane;

$N^I,N^{IV}$-bis[2,2,6,6-tetramethylpiperidin-4-yl]-$N^I,N^{II},N^{III},N^{IV}$-tetrakis[2,4-bis[N-(2,2,6,6-tetramethylpiperidin-4-yl)-dodecylamino]-triazin-6-yl]-1,5,8,12-tetraazadodecane;

$N^I,N^{IV}$-bis[1,2,2,6,6-pentamethylpiperidin-4-yl]-$N^I,N^{II},N^{III},N^{IV}$-tetrakis[2,4-bis[N-(1,2,2,6,6-pentamethylpiperidin-4-yl)-dodecylamino]-triazin-6-yl]-1,5,8,12-tetraazadodecane;

$N^I,N^{IV}$-bis[2,2,6,6-tetramethylpiperidin-4-yl]-$N^I,N^{II},N^{III},N^{IV}$-tetrakis[2,4-bis[N-(1,2,2,6,6-pentamethylpiperidin-4-yl)-butylamino]-triazin-6-yl]-1,5,8,12-tetraazadodecane;

$N^I,N^{IV}$-bis[2,2,6,6-tetramethylpiperidin-4-yl]-$N^I,N^{II},N^{III},N^{IV}$-tetrakis[2,4-bis[N-(1,2,2,6,6-pentamethylpiperidin-4-yl)-ethylamino]-triazin-6-yl]-1,5,8,12-tetraazadodecane;

$N^I,N^{IV}$-bis[2,2,6,6-tetramethylpiperidin-4-yl]-$N^I,N^{II},N^{III},N^{IV}$-tetrakis[2,4-bis[N-(1,2,2,6,6-pentamethylpiperidin-4-yl)-dodecylamino]-triazin-6-yl]-1,5,8,12-tetraazadodecane Compounds of formula (I) of particular interest are:

$N^I,N^{II},N^{III}$-tris[2-(N-(2,2,6,6-tetramethylpiperidin-4-yl)-butylamino)-4-(bis[2,2,6,6-tetramethylpiperidin-4-yl]amino)-triazin-6-yl]-diethylenetriamine;

$N^I,N^{II},N^{III}$-tris[2-(N-(1,2,2,6,6-pentamethylpiperidin-4-yl)-butylamino)-4-(bis[1,2,2,6,6-pentamethylpiperidin-4-yl]amino)-triazin-6-yl]-diethylenetriamine;

$N^I,N^{II},N^{III},N^{IV}$-tetrakis[2-(N-(2,2,6,6-tetramethylpiperidin-4-yl)-butylamino)-4-(bis[2,2,6,6-tetramethylpiperidin-4-yl]amino)-triazin-6-yl]-1,5,8,12-tetraazadodecane;

$N^I,N^{II},N^{III},N^{IV}$-tetrakis[2-(N-(1,2,2,6,6-pentamethylpiperidin-4-yl)-butylamino)-4-(bis[1,2,2,6,6-pentamethylpiperidin-4-yl]amino)-triazin-6-yl]-1,5,8,12-tetraazadodecane;

$N^I,N^{IV}$-bis[2,2,6,6-tetramethylpiperidin-4-yl]-$N^I,N^{II},N^{III},N^{IV}$-tetrakis[2,4-bis[N-(2,2,6,6-tetramethylpiperidin-4-yl)-butylamino]-triazin-6-yl]-1,5,8,12-tetraazadodecane;

N',N'''-bis[1,2,2,6,6-pentamethylpiperidin-4-yl]-N',N'',N''',N''''-tetrakis[2,4-bis[N-(1,2,2,6,6-pentamethylpiperidin-4-yl)-butylamino]-triazin-6-yl]-1,5,8,12-tetraazadodecane.

The compounds of the present invention may be prepared, for example, in accordance with known procedures (e.g. as described in U.S. Pat. No. 4,108,829 and JP Patent Sho 57-38589 as well as U.S. Pat. Nos. 4,816,507 and 4,997,938), inducing the reaction, in any order and in appropriate molar ratios, of cyanuric chloride with compounds of formula (Va)–(Vc)

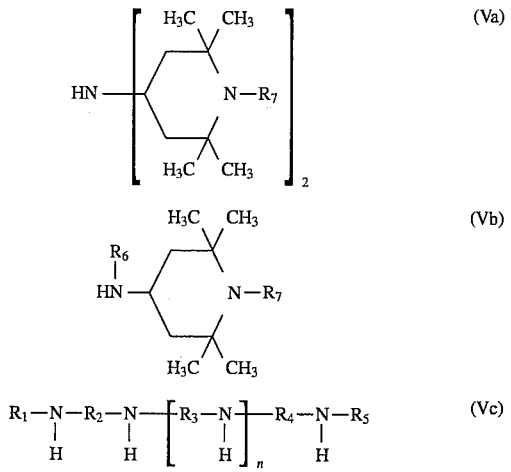

in which $R_7$=H.

The reactions are preferably carried out in an inert organic solvent, for example toluene, xylene, trimethylbenzene, t-amyl alcohol, 1,2-dichloroethane or mixtures in any ratio of t-amyl alcohol with the said solvents, in the presence of a preferably inorganic base, such as for example sodium or potassium hydroxide or carbonate, at a temperature between −20° C. and 200° C., preferably between −10° C. and 180° C.

Compounds of formula (I) with $R_7$=H can be obtained in this way, from which compounds it is possible subsequently to obtain corresponding compounds with $R_7 \neq H$ according to known procedures. Compounds of formula (Va) and (Vb) can be prepared by means of known procedures; compounds of formula (Vc) are commercially available or can be prepared by means of known techniques.

As indicated at the outset, the compounds of the present invention are very effective in enhancing the resistance of organic materials, in particular synthetic polymers and copolymers, to light, heat and oxidation.

Examples of such organic materials which can be stabilized are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethy-lidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylirene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydanloins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose buryrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The compounds of formula (I) are particularly well suited to enhance the resistance to light, heat and oxidation of polyolefins, in particular polyethylene and polypropylene.

The compounds of formula (I) may be used in mixture with organic materials in various proportions, depending on the nature of the material requiring stabilization, its final use and the presence of other additives.

In general, it is suitable to use for example 0.01 to 5 wt % of a compound of the formula (I) based on the weight of the material requiring stabilization, preferably between 0.05 and 1%.

In general, compounds of formula (I) may be incorporated in polymer materials before, during and after the polymerization or crosslinking of the said materials.

Compounds of formula (I) can in general be incorporated in polymer materials in pure form or encapsulated in wax, oils or polymers.

The compounds of formula (I) can be incorporated in polymer materials by different procedures, such as dry mixing in powder form or wet mixing in solution or suspension or in the masterbatch form; in such operations the polymer may be used in the form of a powder, granulate, solution, suspension or as a latex.

The materials stabilized with the compounds of formula (I) may be used for the preparation of moulded objects, films, tapes, as a single filament, as fibre, lacquer or in similar forms.

Other conventional additives for synthetic polymers, such as anti-oxidants, UV absorbers, nickel stabilizers, pigments, fillers, plasticizers, corrosion inhibitors and metal deactivators may, where appropriate, be added to mixtures of the compounds of formula (I) with organic materials.

Specific examples of the additives which may be used in mixture with the compounds of formula (I) are listed below in detail:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-di-phenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl) disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-omethylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-burtyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmer-captobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl) butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)-bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-di-methylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6- hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4° hydroxymethyl-1-phospha-2,6,7-trioxabicyclo-[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

1.18. Ascorbic acid (vitamin C)

1.19. Amine antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylamino-phenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, Bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-di-hydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazin, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV absorbers and light stabilisers 2.1.2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzole, 2-(2'-hydroxy-5'-(1,1,3,3-tetramethylbutyl)phenyl)benzo-triazole, 2-(3',5'-di-tert-butyl-2'-hydroxyphenyl)-5-chloro-benzotriazole, 2-(3'-tert-butyl-2'-hydroxy-5'-methylphenyl)-5-choloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-ditert-amyl-2'-hydroxyphenyl)benzotriazole, 2-(3',5'-bis-(α,α-dimethylbenzyl)-2'hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzothiazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—$CH_2CH_2$—$COO(CH_2)_3$—$]_2$, where R=3'-tert-butyl-4'-hydroxy-5'-2H-benzotriazol-2-ylphenyl.

2.2.2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoy)resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates., for example ethyl α-cyano-β,β-diphenylacrylate, isooctyl α-cyano- β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-1auroylo5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl)n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dion, bis(1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetra- methyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropyl-amino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(12,2,6,6-pentamethyl-4-piperidyl)pyrrolidine-2,5-dione, a mixture of 4-hexadecyloxy and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5otriazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-1,2,2,6,6-petamenthyl-4-piperidyl)-n-dodecylsuccinimid, 2-undecyl-7,7,9,9-tetramethyl-1-oxa-3,8-diaza-4-oxo-spiro[4,5] decane, a reaction product of 7,7,9,9-tetramethyl-2-cycloundecyl-1-oxa-3,8-diaza-4-oxospiro [4,5]decane und epichlorohydrin.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8. 2-(2-Hydroxyphenyl)-1,3,5-trizines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhyclrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphires, phenyl dialkyl phosphites, tris(nonylphenyl) phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl)methylphosphite, bis(2,4-di-tert-butyl-6-methylphenyl)ethylphosphite.

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydro genaral tallow amine.

6. Nitrones, for example, N-benzyl-alpha-phenyl-nitrone, N-ethyl-alpha-methyl-nitrone, N-octy12alpha-heptyl-nitrone, N-lauryl-alpha-undecyl-nitrone, N-tetradecyl-alpha-tride-cyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-hepta-decyl-alpha-heptadecyl-nitrone, N-octadecyl-alpha-hexadecyl-nitrone, nitrone derived from N,N-dialkylhydroxylamine derived from hydrogenareal tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl elisulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers ("ionomers").

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. Nos. 4,325,863, 4,338,244, 5,175,312, 5,216,052, 5,252,643, DE-A-4 316 611, DE-A-4 316 622, DE-A-4 316 876, EP-A-0 589 839 or EP-A-0 591 102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]-phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

The compounds of the formula (I) can also be used as stabilizers, especially as light stabilizers, for almost all materials known in the art of photographic reproduction and other reproduction techniques as e.g. described in Research Disclosure 1990, 31429 (page 474 to 480).

Several examples of the preparation and use of the compounds of the formula (I) are reported for more detailed illustration of the present invention; these examples are given solely for illustrative purposes and do not imply any restriction.

The compounds of formula (I) are especially useful for stabilizing polypropylene fibres. The compounds of the following Examples 1, 3, 4 and 5 are of particular interest.

EXAMPLE 1

Preparation of the compound of the formula

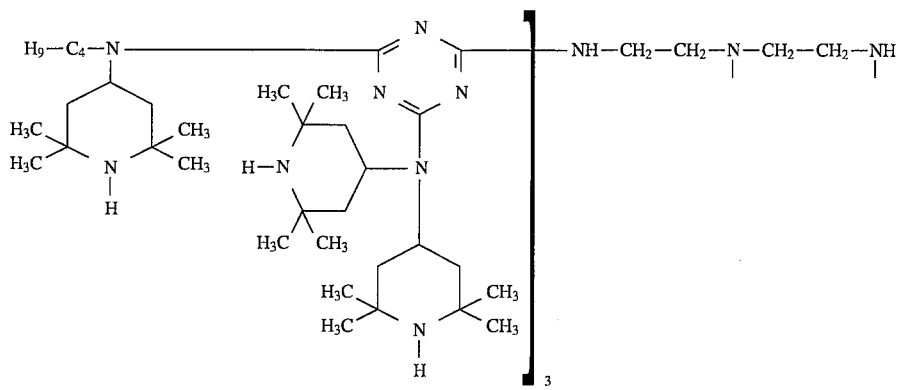

A solution consisting of 286.4 g (1 mole) N-(2,2,6,6-tetramethyl-4-piperidyl)-2,2,6,6-tetramethyl-4-piperidylamine in 550 ml 1,2-dichloroethane is added slowly at 0° C. to a mixture of 184.5 g (1 mole) cyanuric chloride in 1000 ml 1,2-dichloroethane. When the addition is complete, the mixture is stirred for 2 h at room temperature, then cooled to 10° C. and a solution containing 40 g (1 mole) sodium hydroxide in 120 ml water added to it.

The mixture is stirred for 2 h at room temperature, filtered and the solid residue washed twice with 300 ml water. 1500 ml 1,2-dichlorethane, 34.4 g (0.33 moles) diethylenetriamine and 4 g (1 mole) sodium hydroxide dissolved in 120 ml water are then added at room temperature.

The mixture thus obtained is heated to 80° C. for 2 h, the aqueous phase separated and the organic layer washed with water.

After evaporation of the solvent, 212.4 g (1 mole) N-butyl-2,2,6,6-tetramethyl-4-piperidylamine, 80 g (2 moles) sodium hydroxide and 2000 ml trimethylbenzene are added; the mixture is then heated under reflux for 12 h, eliminating the water of reaction by azeotropic distillation. The mixture is filtered, the organic solution washed with water, the solvent evaporated and the residue crystallized from acetonitrile. A product is obtained with a melting point of 166°–173° C.

Analysis for $C_{106}H_{199}N_{27}$ Calculated: C=68.75%; H=10.83%; N=20.42% Found: C=68.47%; H=10.81%; N=20.06%

EXAMPLE 2

By proceeding as described in Example 1 but with the use of 1,5,8,12-tetraazadodecane in place of diethylenetriamine, the compound of the following formula is obtained

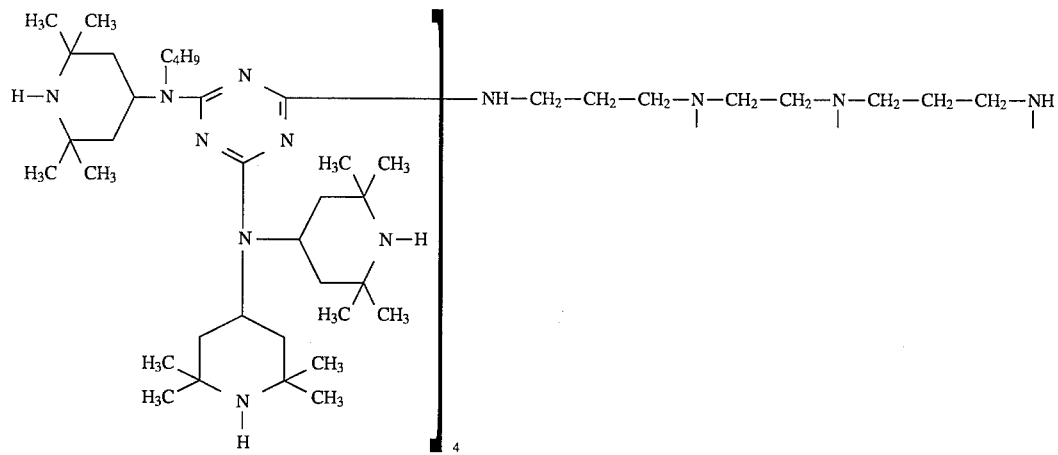

with a melting point of 178°–183° C.

Analysis for $C_{144}H_{270}ON_{36}$ Calculated: C=69.02%; H=10.86%; N=20.12% Found: C=67.87%; H=10.66%; N=19.82%

EXAMPLE 3

Preparation of the compound of the formula

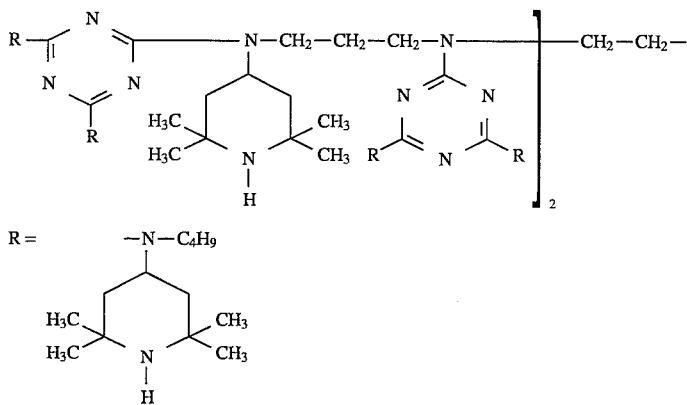

100 g (0.47 moles) N-butyl-2,2,6,6-tetramethyl-4-piperidylamine are added over 1 h to 87 g (0.47 moles) cyanuric chloride in 600 ml trimethylbenzene. On conclusion of the addition, the mixture is stirred for 1 h at room temperature. After cooling to 5° C., 100 ml aqueous solution containing 20 g (0.5 moles) sodium hydroxide is added; the mixture thus obtained is maintained for 1 h at room temperature, the phases separated and the organic layer washed with water.

53.1 g (0.12 moles) 1,12-bis(2,2,6,6-tetramethyl-4-piperidyl)-1,5,8,12-tetraazadodecane, dissolved in 200 ml trimethylbenzene, and 68 g (0.5 mole) potassium carbonate, are then added and the mixture is heated at 80° C. for 6 h.

After the addition of 40 g (1 mole) sodium hydroxide and 100 g (0.47 moles) N-butyl-2,2,6,6-tetramethyl-4-piperidylamine, the mixture is heated under reflux for 16 h. On completion of the reaction, the mixture is washed several times with water and the solvent evaporated, yielding a product having a melting point of 167°–171° C.

Analysis for $C_{142}H_{268}N_{34}$ Calculated: C=69.56%; H=11.02%; N=19.42% Found: C=69.26%; H=10.83%; N=19.30%

EXAMPLE 4

Preparation of the compound of the formula

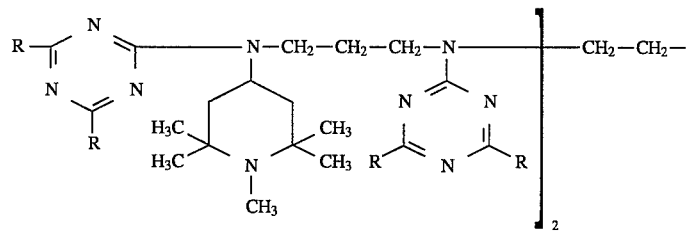

R = 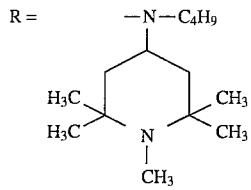

A solution containing 4.3 g (0.144 moles) formaldehyde (containing no methanol) and 6.6 g (0.144 moles) formic acid in 50 ml water is added over a period of 2 h to a solution, heated under reflux, of 29.4 g (0.012 moles) of the product from Example 3 in 150 ml xylene, eliminating simultaneously, by azeotropic evaporation, the added water and the water of reaction.

After cooling to room temperature, a solution of 5.8 g NaOH in 50 ml water is added, the mixture is stirred for 15 min and the aqueous phase separated. The organic phase is washed with water and the solvent evaporated, yielding a product having a melting point of 177°–180° C.

Analysis for $C_{172}H_{228}N_{34}$ Calculated: C=70.43%; H=11.20%; N=18.37% Found: C=69.58%; H=10.98%; N=18.28%

EXAMPLE 5

Operating as described in Example 4, but using the product from Example 1 in place of the product from Example 3 and adjusting to the appropriate molar ratios yields a product of formula NH—CH$_2$CH$_2$—N—CH$_2$CH$_2$—NH
  |          |           |
  R          R           R R = 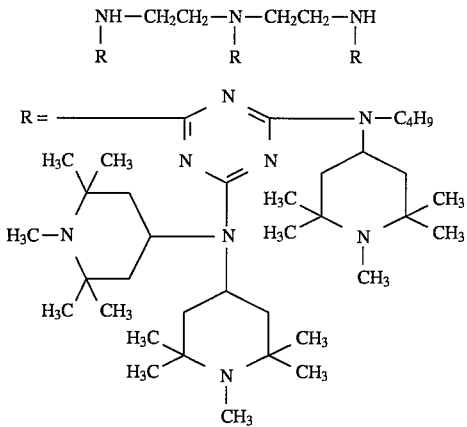

having a melting point of 203°–208° C.

Analysis for $C_{115}H_{217}N_{27}$ Calculated: C=69.83%; H=11.06%; N=19.12% Found: C=69.76%; H=10.94%; N=19.02%

EXAMPLE 6

Operating as described in Example 4 but using the product from Example 2 in place of the product from Example 3 and adjusting to the appropriate molar ratios yields a compound of the formula

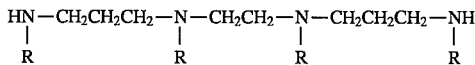

R = 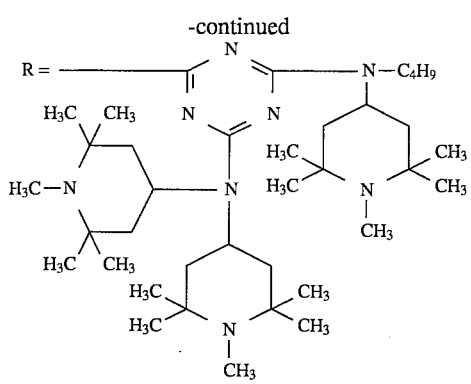

having a melting point of 212°–218° C.

Analysis for $C_{156}H_{294}N_{36}$ Calculated: C=70.06%; H=11.08%; N=18.85% Found: C=69.50%; H=10.92%; N=18.85%

EXAMPLE 7

Stabilizing action against light in polypropylene fibres. 2.5 g of the product from Example 3, 1 g tris(2,4-di-t-butylphenyl) phosphite, 0.5 g monoethyl calcium 3,5-di-t-butyl-4-hydroxybenzylphosphonate, 1 g calcium stearate and 2.5 g titanium dioxide are mixed in a low-speed mixer with 1000 g polypropylene in powder form having a melt index =12 g/10 min (measured at 230° C and 2.16 kg).

The mixtures are extruded at 200°–230° C. in order to obtain polymer granules which are then converted into fibres, using semi-industrial apparatus (®Leonard-Sumirago (VA) Italia), operating under the following conditions:

extruder temperature: 200°–230° C.

temperature of the head: 255°–260° C.

stretch ratio: 1:3.5 filament under density: 11 dtex.

The fibres thus prepared are exposed, after mounting on white cardboard, in a Weather-O-Meter, model 65WR (ASTM D2565-85) with a black panel temperature of 63° C. The residual tenacity is measured on samples taken after exposure to light for different periods of time, using a constant-velocity dynamometer and the time in hours required to reduce the initial tenacity by 50% ($T_{50}$) calculated from the values obtained. For comparison purposes, fibres, which have been prepared under the conditions described above but without the addition of the stabilizing agents according to the present invention are exposed. The results are shown in Table 1.

TABLE 1

| Stabilizer | $T_{50}$ (hours) |
|---|---|
| Without stabilizer | 240 |
| Compound from Example 3 | 1900 |

EXAMPLE 8

Stabilizing action against light in polypropylene fibres after thermal treatment.

Fibres prepared as in Example 7 are exposed to 120° C. for 20 min in an oven and then, after mounting on white cardboard, exposed in a Weather-O-Meter, model 65WR (ASTM D 2565-85) at a black panel temperature of 63° C.

The residual ultimate tenacity is measured on samples taken after exposure to light for different periods of time, using a constant-velocity dynamometer and the time in hours required to reduce the initial tenacity by 50% ($T_{50}$) calculated from the values obtained. For comparison purposes, fibres, which have been prepared under the conditions described above but without the addition of the stabilizing agents according to the present invention are also exposed.

The results are shown in Table 2.

TABLE 2

| Stabilizer | $T_{50}$ (hours) |
| --- | --- |
| Without stabilizer | 150 |
| Compound from Example 3 | 1802 |

EXAMPLE 9

Stabilizing action against light in polypropylene fibres 2.5 g of the product indicated in Table 3, 1 g tris(2,4-di-t-butylphenyl)phosphite, 0.5 g monoethyl calcium 3,5-di-t-butyl-4-hydroxybenzylphosphonate, 1 g calcium stearate and 2.5 g titanium dioxide are mixed in a low-speed mixer with 1000 g polypropylene in powder form having a melt index=12 g/10 min (measured at 230° C. and 2.16 kg). The mixtures are extruded at 200°–230° C. in order to obtain polymer granules which are then converted into fibres, using semi-industrial apparatus (®Leonard-Sumirago (VA) Italia), operating under the following conditions:

extruder temperature: 200°–230° C.

temperature of the head: 255°–260° C.

stretch ratio: 1:3.5 filament linear density: 11 dtex.

The fibres thus prepared are exposed, after mounting on white cardboard, in a Weather-O-Meter, model 35WR (ASTM D2565-85) with a black panel temperature of 63° C.

The residual tenacity is measured on samples taken after exposure to light for different periods of time, using a constant-velocity dynamometer and the time in hours required to reduce the initial tenacity by 50% ($T_{50}$) calculated from the values obtained. For comparison purposes, fibres, which had been prepared under the conditions described above but without the addition of the stabilizing agents according to the present invention were also exposed. The results are shown in Table 3.

TABLE 3

| Stabilizer | $T_{50}$ (hours) |
| --- | --- |
| Without stabilizer | 250 |
| Compound from Example 4 | 2100 |
| Compound from Example 5 | 2510 |
| Compound from Example 6 | 2240 |

EXAMPLE 10

Stabilizing action against light in polypropylene fibres after thermal treatment Fibres prepared as in Example 9 are exposed in an oven to 120° C. for 20 min and then, after mounting on white cardboard, exposed in a Weather-O-Meter, model 35WR (ASTM D 2565-85) at a black panel temperature of 63° C.

The residual tenacity is measured on samples taken after exposure to light for different periods of time, using a constant-velocity dynamometer and the time in hours required to reduce the initial tenacity by 50% ($T_{50}$) calculated from the values obtained. For comparison purposes, fibres, which have been prepared under the conditions described above but without the addition of the stabilizing agents according to the present invention are also exposed. The results are shown in Table 4.

TABLE 4

| Stabilizer | $T_{50}$ (hours) |
| --- | --- |
| Without stabilizer | 150 |
| Compound from Example 4 | 2130 |
| Compound from Example 5 | 2220 |
| Compound from Example 6 | 2060 |

EXAMPLE 11

Stabilizing action against light in polypropylene tapes 1 g of the compound referred to in Table 5, 1.0 g tris(2,4-di-t-butylphenyl) phosphite, 0.5 g pentaerythritol tetrakis[3-(3,5-di-t-butyl-4-hydroxyphenyl)propionate]and 1 g calcium stearate are mixed in a low-speed mixer with 1000 g polypropylene in powder form, having a melt index= 12 g/10 min (measured at 230° C. and 2.16 kg).

The mixtures are extruded at 200°–220° C. in order to obtain polymer granules which are then converted into stretched tapes having a thickness of 50 μm and a width of 2.5 mm, using semi-industrial apparatus (®Leonard-Sumirago (VA) Italia), operating under the following conditions:

extruder temperature: 210°–230° C.

temperature of the head: 240°–260° C.

stretch ratio: 1:6

The tapes material thus prepared is exposed, after mounting on white cardboard, in a Weather-O-Meter, model 65WR (ASTM D2565-85) with a black panel temperature of 63° C. The residual tenacity is measured on samples taken after exposure to light for different periods of time, using a constant-velocity dynamometer, and the time (in hours) required to reduce the initial tenacity by 50% ($T_{50}$) calculated from these values. For comparison purposes, tapes which have been prepared under the conditions described above but without the addition of the stabilizing agents are also exposed. The results are shown in Table 5.

TABLE 5

| Stabilizer | $T_{50}$ (hours) |
| --- | --- |
| Without stabilizer | 320 |
| Compound from Example 3 | 1800 |

EXAMPLE 12

Stabilizing action against light in polypropylene tapes.

Operating as described in Example 11 but with the use of a 35WR Weather-O-Meter (ASTM D 2565-85) yields the results shown in Table 6.

TABLE 6

| Stabilizer | $T_{50}$ (hours) |
| --- | --- |
| Without stabilizer | 340 |
| Compound from Example 1 | 2100 |
| Compound from Example 5 | 2000 |

What is claimed is:

1. A compound of formula (I)

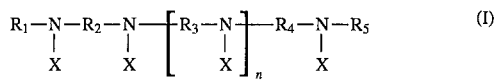

in which n is zero or 1;

X denotes a group of formula (II),

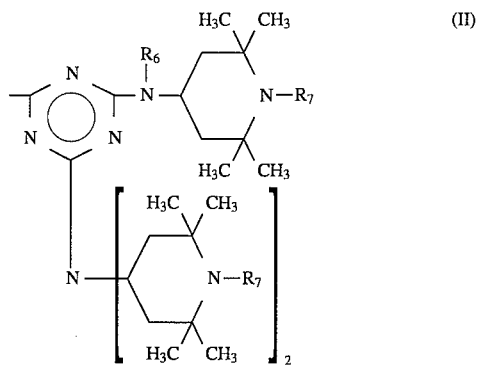

$R_1$ and $R_5$, which may be identical or different, are hydrogen, $C_1$–$C_{18}$alkyl, $C_5$–$C_{12}$cycloalkyl, unsubstituted or substituted with 1, 2 or 3 $C_1$–$C_4$alkyls;

$C_7$–$C_9$phenylalkyl, unsubstituted or substituted on the phenyl with 1, 2 or 3 $C_1$–$C_4$alkyls; or a group of formula (III)

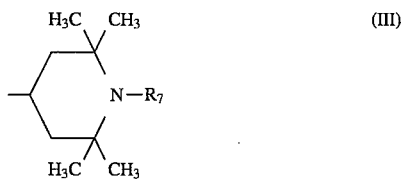

$R_2$, $R_3$ and $R_4$, which may be identical or different, are $C_2$–$C_{12}$alkylene;

$R_6$ is hydrogen, $C_1$–$C_{18}$alkyl, $C_5$–$C_{12}$cycloalkyl, unsubstituted or substituted with 1, 2 or 3

$C_1$–$C_4$alkyls, $C_3$–$C_6$alkenyl, $C_7$–$C_9$phenylalkyl, unsubstituted or substituted on the phenyl with 1, 2 or 3 $C_1$–$C_4$alkyls;

$R_7$ is hydrogen, $C_1$–$C_8$alkyl, O, OH, $CH_2CN$, $C_1$–$C_{18}$alkoxy, $C_5$–$C_{12}$cycloalkoxy, $C_3$–$C_6$alkenyl, $C_7$–$C_9$phenylalkyl, unsubstituted or substituted on the phenyl with 1, 2 or 3 $C_1$–$C_4$alkyls; or $R_7$ is an aliphatic $C_1$–$C_8$acyl.

2. A compound of formula (I) according to claim 1, in which $R_7$ is hydrogen, $C_1$–$C_4$alkyl, OH, $C_6$–$C_{12}$alkoxy, $C_5$–$C_8$cycloalkoxy, allyl, benzyl or acetyl.

3. A compound of formula (I) according to claim 1, in which $R_7$ is hydrogen or methyl.

4. A compound of formula (I) according to claim 1, in which $R_1$ and $R_5$, which may be identical or different, are hydrogen, $C_1$–$C_{12}$alkyl, $C_5$–$C_7$cycloalkyl or $C_7$–$C_9$phenylalkyl; $R_2$, $R_3$ and $R_4$, which may be identical or different, are $C_2$–$C_6$alkylene and $R_6$ is hydrogen, $C_1$–$C_{12}$alkyl, $C_5$–$C_7$cycloalkyl, $C_3$–$C_6$alkenyl or $C_7$–$C_9$phenylalkyl.

5. A compound of formula (I) according to claim 1, in which $R_1$ and $R_5$, which may be identical or different, are hydrogen, $C_1$–$C_6$alkyl, cyclohexyl or benzyl; $R_2$, $R_3$ and $R_4$, which may be identical or different, are $C_2$–$C_6$alkylene and $R_6$ is hydrogen, $C_1$–$C_6$alkyl, cyclohexyl, allyl or benzyl.

6. A compound of formula (I) according to claim 1, in which $R_1$ and $R_5$, which may be identical or different, are hydrogen or $C_1$–$C_4$alkyl; $R_2$, $R_3$ and $R_4$, which may be identical or different, are $C_2$–$C_3$alkylene; $R_6$ is $C_1$–$C_4$alkyl and $R_7$ is hydrogen or methyl.

7. A compound of formula (I) according to claim 1, in which the said compound is $N^I,N^{II},N^{III}$-tris[2(N-(2,2,6,6-tetramethylpiperidin-4-yl)butylamino)-4-(bis[2,2,6,6-tetramethlpiperidin-4-yl]amino)-triazin-6-yl]-diethylenetriamine;

$N^I, N^{II}, N^{III}$-tris[2-(N-(1,2,2,6,6-pentamethylpiperidin-4-yl)butylamino)-4-(bis[1,2,2,6,6-pentamethlpiperidin-4-yl]amino)-triazine-6-yl]-diethylenetriamine;

$N^I,N^{II},N^{III},N^{IV}$-tetrakis[2-(N-(2,2,6,6-tetramethylpiperidin-4-yl)-butylamino)-4-bis[2,2,6,6-tetramethylpiperidin-4-yl]amino)-triazin-6-yl]-1,5,8,12-tetraazadodecane; or $N^I,N^{II},N^{III},N^{IV}$-tetrakis[2-(N-(1,2,2,6,6-pentamethylpiperidin-4-yl)butylamino)-4-(bis[1,2,2,6,6-pentamethylpiperidin-4-yl]amino)-triazin-6-yl]-1,5,8,12-tetraazadodecane.

8. A composition comprising an organic material subject to degradation induced by light, heat or oxidation and at least one compound of formula (I) according to claim 1.

9. A composition according to claim 8, in which the organic material is a synthetic polymer.

10. A composition according to claim 9 comprising, in addition to the compound of formula (I), other additives conventionally present in synthetic polymers selected from the group consisting of antioxidants, UV absorbers, nickel stabilizers, pigments, plasticizers, corrosion inhibitors and metal deactivators.

11. A composition according to claim 8, in which the organic polymer is polyethylene or polypropylene.

12. A method for stabilizing an organic material against degradation induced by light, heat or oxidation, which comprises incorporating into said organic material at least one compound of the formula (I) according to claim 1.

* * * * *